US012564198B2

(12) United States Patent
Patin et al.

(10) Patent No.: US 12,564,198 B2
(45) Date of Patent: Mar. 3, 2026

(54) METHOD FOR MANUFACTURING SN-2 PALMITIC TRIACYLGLYCEROLS

(71) Applicant: SOCIETE DES PRODUITS NESTLE S.A., Vevey (CH)

(72) Inventors: Amaury Patin, Lausanne (CH); Tim Börner, Epalinges (CH); Lars Dahlgren, Lund (SE); Francesca Giuffrida, Mezieres (CH)

(73) Assignee: Societe des Produits Nestle S.A., Vevey (CH)

( * ) Notice: Subject to any disclaimer, the term of this patent is extended or adjusted under 35 U.S.C. 154(b) by 471 days.

(21) Appl. No.: 17/995,415

(22) PCT Filed: Apr. 6, 2021

(86) PCT No.: PCT/EP2021/058843
§ 371 (c)(1),
(2) Date: Oct. 4, 2022

(87) PCT Pub. No.: WO2021/204746
PCT Pub. Date: Oct. 14, 2021

(65) Prior Publication Data
US 2023/0189834 A1 Jun. 22, 2023

(30) Foreign Application Priority Data

Apr. 9, 2020 (EP) ..................................... 20169026

(51) Int. Cl.
*A23D 9/04* (2006.01)
*C11C 3/00* (2006.01)
*C12P 7/6454* (2022.01)

(52) U.S. Cl.
CPC ................ *A23D 9/04* (2013.01); *C11C 3/003* (2013.01); *C12P 7/6454* (2013.01)

(58) Field of Classification Search
CPC .......... A23D 9/04; C11C 3/003; C12P 7/6454
See application file for complete search history.

(56) References Cited

U.S. PATENT DOCUMENTS

2009/0123982 A1    5/2009  Harris et al.
2016/0227810 A1*   8/2016  Akoh ........................ C11C 3/08

FOREIGN PATENT DOCUMENTS

| CN | 102776077 A | 11/2012 |
| CN | 105028659 A | 11/2015 |
| CN | 105483170 A | 4/2016 |
| CN | 107549313 A | 1/2018 |
| CN | 108244273 A | 7/2018 |
| CN | 109468349 A | 3/2019 |
| CN | 109988674 A | 7/2019 |
| JP | H07107904 A | 4/1995 |

(Continued)

OTHER PUBLICATIONS

Chinese Office Action for Appl No. 202180025383.6 dated Dec. 2, 2024, 10 pages.

(Continued)

*Primary Examiner* — Erik Kashnikow
*Assistant Examiner* — Assaf Zilbering
(74) *Attorney, Agent, or Firm* — K&L Gates LLP

(57) ABSTRACT

The present invention concerns an enzymatic process for the preparation of a triglyceride ingredient comprising triglycerides present in human breast milk.

4 Claims, 3 Drawing Sheets

1. Alcoholysis

Tripalmitin + n-butanol $\xrightarrow[\text{lipase}]{\text{Sn-1,3 specific}}$ 2-monopalmitin + butyl-palmitate + n-butanol 2. Intermediate Purification 2-monopalmitin + butyl-palmitate + n-butanol $\xrightarrow[]{\text{Fractionation +}\atop\text{Filtration}}$ 2-monopalmitin butyl-palmitate + n-butanol 3. Esterification 2-monopalmitin + Fatty acid mix $\xrightarrow[\text{lipase}]{\text{Sn-1,3 specific}}$ TAG mix

2 H$_2$O

4. Down-stream Processing

(56)        References Cited

FOREIGN PATENT DOCUMENTS

RU          2469545 C2     12/2012
RU          2635696 C2     11/2017
RU          2703172 C2     10/2019

OTHER PUBLICATIONS

Chinese Office Action for Appl No. 202180025383.6 dated May 1, 2024, 36 pages.
Kallio et al. "Triacylglycerol regioisomers in human milk resolved with an algorithmic novel electrospray ionization tandem mass spectrometry method" Food Chemistry, 2017, vol. 233, pp. 351-360.

Wang et al. "Enzymatic synthesis of structured triacylglycerols rich in 1,3-dioleoyl-2-palmitoylglycerol and 1-bleoyl-2-palmitoyl-3-lineoylglycerol in a solvent-free system" LWT—Food Science and Technology, 2020, vol. 118, 7 pages.
Schmid et al., Highly Selective Synthesis of 1,3-Oleoyl-2-Palmitoylglycerol by Lipase Catalysis Biotechnology and Bioengineering, 1999, vol. 64, No. 6, pp. 678-684.
Zuyi et al. "Lipase-catalyzed alcoholysis to concentrate the n-3 polyunsaturated fatty acid of cod liver oil" Enzyme Microb. Technol., 1993, vol. 15, pp. 601-606.
Kuznetsova., "Brackets in the Text of Legal Document as a Linguistic and Cognitive Phenomenon", Russian Philology, Issue No. 03, 2015, pp. 37-43.
Shcheryakov et al., "Biochemistry and Commodity Science of Oilseed Raw Materials", 5th Edition, 2003, p. 51.
Russian Office Action for Appl No. 2022126090/10 dated Jan. 13, 2025, 9 pages.

* cited by examiner

1. <u>Alcoholysis</u>

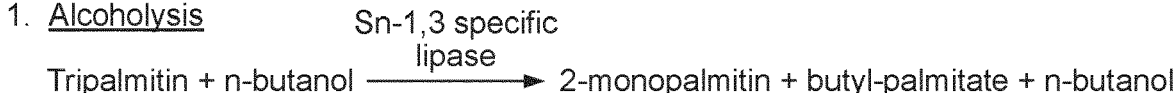

Tripalmitin + n-butanol $\xrightarrow[\text{lipase}]{\text{Sn-1,3 specific}}$ 2-monopalmitin + butyl-palmitate + n-butanol 2. <u>Intermediate Purification</u>

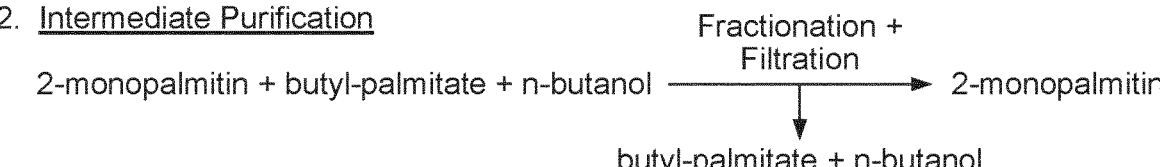

2-monopalmitin + butyl-palmitate + n-butanol $\xrightarrow{\substack{\text{Fractionation +} \\ \text{Filtration}}}$ 2-monopalmitin butyl-palmitate + n-butanol 3. <u>Esterification</u>

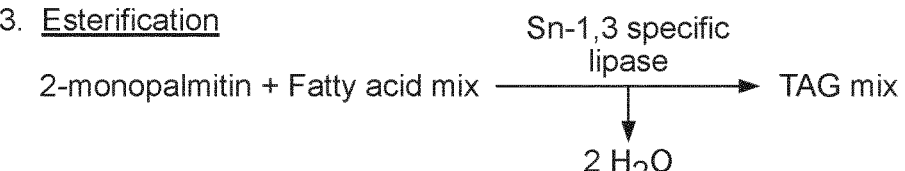

2-monopalmitin + Fatty acid mix $\xrightarrow[\phantom{xx}]{\substack{\text{Sn-1,3 specific} \\ \text{lipase}}}$ TAG mix

2 H$_2$O

4. <u>Down-stream Processing</u>

FIG. 1

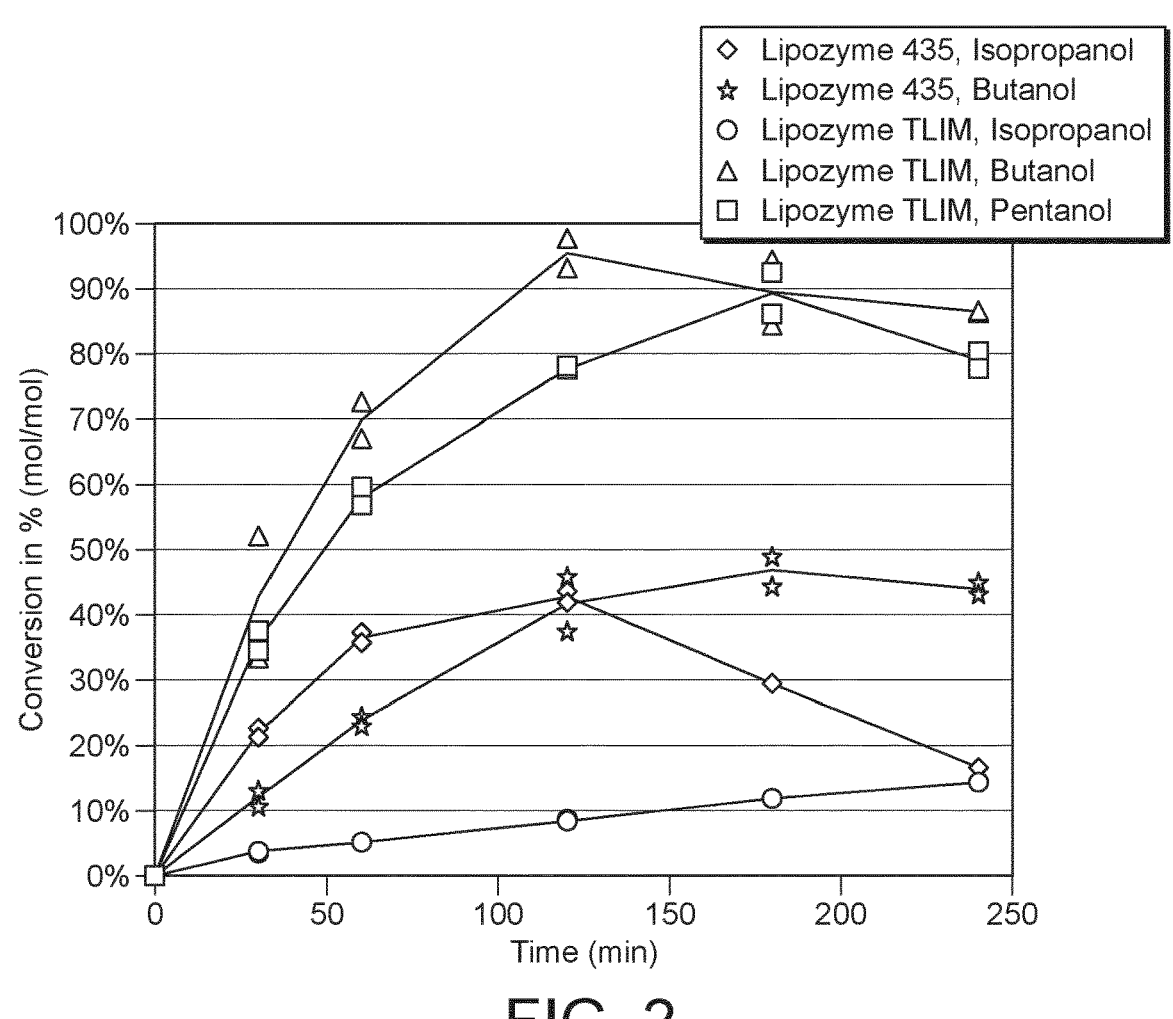

FIG. 2

METHOD FOR MANUFACTURING SN-2 PALMITIC TRIACYLGLYCEROLS

CROSS REFERENCE TO RELATED APPLICATIONS

The present application is a National Stage of International Application No. PCT/EP2021/058843, filed on Apr. 6, 2021, which claims priority to European Patent Application No. 20169026.0, filed on Apr. 9, 2020, the entire contents of which are being incorporated herein by reference.

FIELD OF THE INVENTION

The present invention concerns an enzymatic process for the preparation of an ingredient comprising triglycerides having a palmitic acid residue in position sn-2 which are present in mammalian breast milk, in particular human breast milk.

BACKGROUND OF THE INVENTION

Triacylglycerols/triglycerides (TAG) are the major lipids found in human milk at about 39 g/L and they present a specific regio-specific distribution of fatty acids. The regio-specific distribution of TAG contributes to the nutritional benefits of human milk such as to fatty acid and calcium absorption and their related benefits such as gut comfort.

Infant formula (IF) ingredient design is generally aimed at structural and functional homology with respect to human milk composition and benefits.

In TAG, fatty acids FA esterified in the external positions of the glycerol moiety are named sn-1(3) or alpha FA while FA esterified in the internal position are named sn-2 or beta FA. The FA found in milk are mainly synthetized de novo in the mammary gland or incorporated from FA supplied by the diet. The synthesis of saturated FA is influenced by diet quality and it has been demonstrated that the levels of 6:0-14:0 FA in milk are increased when lactating women consume diets rich in carbohydrate, whereas the content of 18 carbon FA which are derived from the diet, e.g. 18:1 n-9 and 18:2 n-6, are reduced. Among polyunsaturated FA, linoleic (LA, 18:2 n-6) and alpha linolenic acids (ALA, 18:3 n-3) are essential because they are not synthesized in the human body and are, therefore mainly obtained through the diet. They are precursors of arachidonic (20:4 n-6) and docosahexaenoic (22:6 n-3) acids, which are associated with normal brain development especially in early life. Palmitic acid (PA, 16:0) is the most abundant saturated FA in human milk, its level is relatively constant and represents about 20-25% of the total milk FA irrespective of the country of origin and the diets of the mothers, exception made for vegetarians. In human milk, over 70% of the palmitic acid content is esterified in the sn-2 position of TAG. This particularity allowsgreater efficiency of palmitic acid absorption and utilization in breast-fed infants when compared to infants fed with formula in which PA is preferentially esterified in sn-1(3) position of TAG. During digestion, pancreatic lipase releases preferentially the FA in the sn-1(3) positions of the TAG to produce FA and 2-monoacylglycerols. PA esterified in the sn-2 position of monoacylglycerol is mostly absorbed while free PA can react with calcium to form insoluble calcium soaps that are poorly absorbed and are found in the stools. A few studies have observed that the formation of calcium soaps of saturated FA might results in the production of harder stools and constipation in infants [Giuffrida et al, Molecules. 2019 January; 24(1): 22)].

The triglyceride profile of human breast milk lipids has also been the object of investigation [for example in Giuffrida et al, Molecules. 2019 January; 24(1): 22) or H. Kallio et al./Food Chemistry 233 (2017) 351-360] showing that human breast milk contains several triglycerides having the sn-2 position occupied with a palmitic acid residue, for example OPO (18:1-16:0-18:1), OPL (18:1-16:0-18:2), PPO (16:0-16:0-18:1), SPO (18:0-16:0-18:1) and LaPO (12:0-16:0-18:1). Also Kallio et al [H. Kallio et al./Food Chemistry 233 (2017) 351-360] indicates the abundance in human breast milk triglycerides having the sn-2 position occupied with a palmitic acid residue, the most abundant TAGs in a Finnish milk sample being 18:1/16:0/18:1 (9.4% of all TAGs), 18:2/16:0/18:1 (5.4%), 18:1/16:0/12:0 (3.5) 18:1/16:0/18:0 (3.2) and 18:1/16:0/16:0 (3.0%), while the corresponding values of the most abundant compounds in a Chinese sample being 18:2/16:0/18:1 (10.3%) 18:1/16:0/18:1 (7.1%), 18:2/16:0/18:2 (4.5%), 18:1/16:0/18:0 (2.4), 18:1/16:0/16:0 (2.4%) and 18:1/16:0/12:0 (2.1%).

Accordingly, there is a need for a triglyceride based ingredient adapted to prepare the lipid fraction of an infant formula to reflect as closely as possible the human breast milk profile of triglycerides bearing a palmitic acid residue at position sn-2. Such ingredient should, similarly to human breast milk, contain TAGs comprising 70% or more of the palmitic acid content esterified in the sn-2 position and a proportion among the most abundant triglycerides having a palmitic acid in sn-2 position similar to what is found in human breast milk.

There is currently no economically viable method for producing triglycerides adapted for infant formula, ideally containing more than 75% palmitic acid in the sn-2 position (also known as structured lipids). Today, such lipids for infant formula are produced via a single-step, solvent-free enzymatic acidolysis reactions where a fat high in palmitic acid is reacted with oleic acid to produce OPO. This reaction is equilibrium controlled and for high conversion yield high excess (equivalence) of oleic acid needs to be used (Akoh, 2017).

In order to modify the fatty acid composition of triacylglycerols (TAG), a lipase can be used to exchange the fatty acids in the TAG with free fatty acids added to the reaction mixture. For example, by using a sn-1(3) specific lipase on a substrate such as tripalmitin and by adding oleic acid to the reaction mixture, it is possible to produce an OPO ingredient. The main drawback with this approach is that the reaction equilibrium is thermodynamically controlled and an excess of free fatty acid is necessary to push the equilibrium towards the product side. The addition of an excess of free fatty acids drives the process cost (for example in view of additional purification steps) and/or limits the product yields possible. Betapol® and Infat® are two human milk fat mimicking commercial fats (Loders Croklaan, AAK) and are both produced by acidolysis with sn-1(3) specific lipases (Akoh, 2017).

As an alternative to produce structured lipid with high sn-2 palmitic acid content, literature describes the enzymatic two-step approach via the alcoholysis of triglycerides into 2-monoglyceride intermediate (Schmid et al, 1999) and its subsequent esterification with FFA (free fatty acids), which offers higher reaction control, purity and yield. However, this two-step process requires the use of solvents as well as costly starting material (pure tripalmitin) and intermediate purification steps.

Solvents are needed for two reasons: i) solubilization of the triglyceride substrate, i.e., tripalmitin and ii) for dilution to limit inhibition of the lipase by the alcohol (methanol, ethanol) in the alcoholysis step. Intermediate purification is performed either by recrystallization in organic solvents or by distillation under strong vacuum.

In addition, the sn-2 FA content of the TAG starting material for the alcoholysis has a significant impact on the final TAG product profile to maximize sn-2 palmitate in the final product. This is the reason why pure tripalmitin is used in the process.

Thus, for an enzymatic 2-step process to become economically viable and industrially applicable, cost and starting material composition should be taken into consideration. For that, solvent use needs to be reduced or removed and intermediate purification must be simplified, while maintaining high purity and high selectivity of the OPO ingredient obtained, for example a minimum of 50% overall OPO purity and overall a minimum of 70% of the total PA in sn-2 position.

Accordingly, there is also a need to provide a process which would be economically viable and industrially applicable, for the preparation of an ingredient containing TAGS comprising 70% or more of the palmitic acid content esterified in the sn-2 position and a proportion among the most abundant triglycerides having a palmitic acid in sn-2 position similar to what is found in human breast milk.

SUMMARY OF THE INVENTION

The present invention solves the above-mentioned problem by providing a simplified, solvent-free, two-step enzymatic method for producing a triglyceride ingredient with an overall content of palmitic acid in position sn-2 larger than 70%, for example 75% and a proportion among the most abundant triglycerides having a palmitic acid in sn-2 position similar to what is found in human breast milk. This simplified enzymatic process concept offers an economically viable route towards a triglyceride ingredient production.

In one aspect the present invention provides a triglyceride ingredient and a process for the preparation of the triglyceride ingredient as described in the attached claims.

BRIEF DESCRIPTION OF THE DRAWINGS

Additional features and advantages of the present invention are described in, and will be apparent from, the description of the presently preferred embodiments which are set out below with reference to the drawings in which:

FIG. 1 shows a schematic representation on the overall process according to one embodiment of the present invention.

FIG. 2 shows results of Example 1 and reports conversion of 2-monopalmitin over the reaction time for alcoholysis reaction using lipases Lipozyme 435 and TL IM with different alcohols. Conversion calculated as mol 2-monopalmitin/mol initial tripalmitin.

4

DETAILED DESCRIPTION OF THE INVENTION

Definitions

Figure 3:
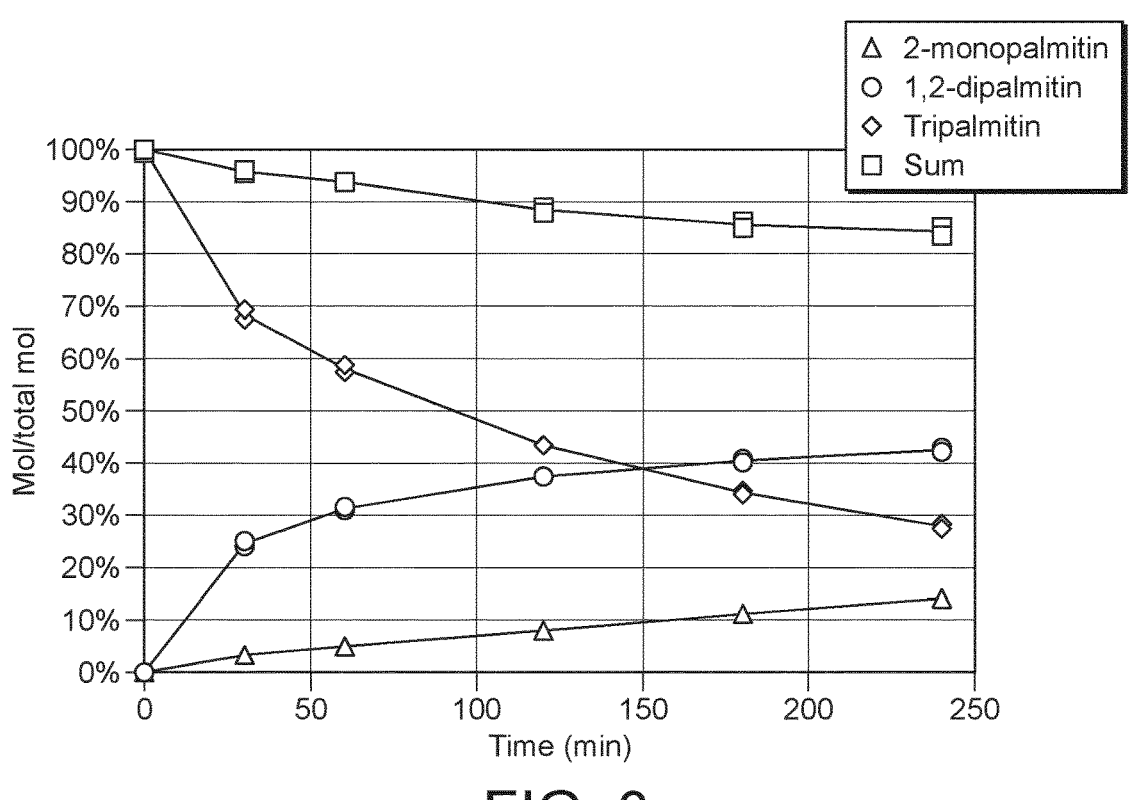
FIG. 3 shows Conversion profile for isopropanolysis of tripalmitin catalyzed by Lipozyme TL IM as described in Example 1.

Within the context of the present invention the term "mammalian breast milk" indicates milk produced during lactation by mammals, for example humans, dogs, cats.

Within the context of the present invention the terms "OPO" or "18:1-16:0-18:1" refers to 1,3-Oleo-2-palmitin and/or 2-(palmitoyloxy)propane-1,3-diyl dioleate and/or (2-(Palmitoyloxy)-1,3-propanediyl (9Z,9'Z)bis(-9-octadecenoate) (CAS number: 1716-07-0)

Within the context of the present invention the term "POO" refers to both 3-(Palmitoyloxy)-1,2-propanediyl (9Z,9'Z)bis(-9-octadecenoate), (OOP, CAS number: 14960-35-1), and/or 1-(Palmitoyloxy)-2,3-propanediyl(9Z,9'Z)bis(-9-octadecenoate), (POO, CAS number: 14863-26-4). It is to be noted that when reference is made to amounts of "POO", this also includes amounts of OOP present in the ingredient.

Within the context of the present invention the terms "OPL", "LPO" or "18:2-16:0-18:1" refers to 1-Oleo-2-palnnito-3-linolein (CAS number: 2534-97-6) and/or 3-Oleo-2-palmito-1-linolein. It is to be noted that when reference is made to amounts of "OPL", "LPO" or "18:2-16:0-18:1, this includes amounts of 1-Oleo-2-palmito-3-linolein and/or 3-Oleo palmito-1-linolein.

Within the context of the present invention the terms "OPP" or "PPO" or "16:0-16:0-18:1" refer to both 1-Oleo-2,3-dipalmitin and/or 3-Oleo-1,2-dipalmitin (CAS number: 1867-91-0). It is to be noted that when reference is made to amounts of "OPP" or "PPO" or "16:0-16:0-18:1", this includes amounts of 1-Oleo-2,3-dipalmitin and/or 3-Oleo-1,2-dipalmitin.

Within the context of the present invention the terms "OPS", "SPO" or "18:0-16:0-18:1" refers to both 2-palmito-3-stearo-1-olein and/or 2-palmito-1-stearo-3-olein (CAS number: 35984-52-2). It is to be noted that when reference is made to amounts of "OPS", "SPO" or "18:0-16:0-18:1", this includes amounts of 2-palmito-3-stearo-1-olein and/or 2-palmito-1-stearo-3-olein.

Within the context of the present invention the terms "OPLa", "LaPO" or "12:0-16:0-18:1" refers to both 1-oleo-2-palmito-3-laurin and/or 3-Oleo-2-palmito-1-laurin (CAS number: 120932-38-9). It is to be noted that when reference is made to amounts of "OPLa", "LaPO" or "12:0-16:0-18:1", this includes amounts of 1-oleo-2-palmito-3-laurin and/or 3-Oleo-2-palmito-1-laurin.

Within the context of the present invention the terms "OPM", "MPO" or "(18:1-16:0-14:0)" refer to 1-oleo-2-palmito-3-myristin and/or 3-Oleo-2-palmito-1-myristin (CAS number: 110585-93-8). It is to be noted that when reference is made to amounts of "OPM" "MPO" or "(18:1-16:0-14:0)", this includes amounts of 1-oleo-2-palmito-3-myristin and/or 3-Oleo-2-palmito-1-myristin.

Within the context of the present invention the terms "OPPa", "PaPO" or "(16:1-16:0-18:1)" refer to 1-oleo-2-palmito-3-palmitolein and/or 3-Oleo-2-palmito-1-palmitolein (CAS number: 114356-98-8). It is to be noted that when reference is made to amounts of "OPPa", "PaPO" or "(16:1-16:0-18:1)", this includes amounts of 1-oleo-2-palmito-3-palmitolein and/or 3-Oleo-2-palmito-1-palmitolein.

Within the context of the present invention the terms "LPP", "PPL" or "(16:0-16:0-18:2)" refers to 1,2-Di-palmito-3-linolein and/or 2,3-Dipalmito-1-linolein (CAS number: 2535-35-5). It is to be noted that when reference is made to amounts of "LPP", "PPL" or "(16:0-16:0-18:2)", this includes amounts of 1,2-Dipalmito-3-linolein and/or 2,3-Dipalmito-1-linolein.

Within the context of the present invention the term "LPL" or "(18:2-16:0-18:2)" refers to 2-Palmito-1,3-dilinolein (CAS number: 2190-16-1).

Within the context of the present invention the terms "LPPa", "PaPL" or "(16:1-16:0-18:2)" refer to 3-linoleo-2-palmito-1-palmitolein and/or 1-linoleo-2-palmito-3-palmitolein (CAS number: 907216-76-6). It is to be noted that when reference is made to amounts of "LPPa", "PaPL" or "(16:1-16:0-18:2)" this includes amounts of 3-linoleo-2-palmito-1-palmitolein and/or 1-linoleo-2-palmito-3-palmitolein.

Within the context of the present invention, the term "OPO Ingredient" or "OPO enriched Ingredient" or "1,3-Olein-2-palmitin ingredient" or simply "OPO" identifies an edible ingredient comprising 1,3-Olein-2-palmitin (OPO) with purity higher than 50 g/100 g of the ingredient. In one embodiment of the present invention, the OPO ingredient prepared according to the process also has a content of palmitic acid in sn-2 position which is equal or higher than 70% of total palmitic content.

Within the context of the present invention, the term "TAG" means Triacylglycerols or triglycerides.

Within the context of the present invention, the term "TAG Ingredient" or "sn-2 palmitic TAG ingredient" or "TAG enriched Ingredient" or "triglyceride ingredient" or "synthetic triglycerides composition" identifies an edible composition of synthetic origin comprising triglycerides, such ingredient having a content of palmitic acid in sn-2 position which is equal or higher than 70% of total palmitic content and having a customized profile of the triglycerides which have a palmitic acid residue at position sn-2.

Within the context of the present invention, the term "triglyceride fat blend" indicates a mixture of triglycerides which is intended for use in Infant formulas and which is obtainable by admixing the triglyceride ingredient of the present invention with a vegetable oil fraction which contains limited amounts of palmitic acid.

Within the context of the present invention, the term "triglycerides enriched in palmitic acid at sn-2 position" means triglycerides and/or triglyceride ingredient wherein a proportion higher than 70% of sn-2 positions in the triglycerides backbone is occupied by palmitic acid residues. In one embodiment, the triglycerides enriched in palmitic acid at sn-2 position have a proportion of sn-2 positions in the triglyceride backbone occupied by palmitic acid residues which is higher than 80%. In one embodiment, the triglycerides enriched in palmitic acid at sn-2 position is a palm oil fraction enriched in triglycerides containing palmitic acid, such as for example CristalGreen® (Bunge Loders Croklaan) which has a content of 60% w/w tripalmitin and wherein the a proportion of sn-2 positions in the triglyceride backbone occupied by palmitic acid residues which is higher than 80%.

Within the context of the present invention, the term "alcoholysis" means the transesterification reaction of fatty acids present in a triglyceride with an alcohol (methanol, ethanol, butanol . . . ) by the action of a selective enzyme. This reaction leads to the formation of monoglycerides and fatty acid esters of the respective alcohol.

Within the context of the present invention, the term "lipase" or "sn-1,3 lipase" means a hydrolytic enzyme that acts on ester bonds (EC 3.1) and belongs to the class of carboxylic-ester hydrolases (EC 3.1.1), and more specifically possesses a high regio-selectivity for hydrolyzing the sn-1 and sn-3 ester bond in a triglyceride backbone. Lipases with high 1,3 selectivity can be sourced, for example, from *Candidata antarctica* (lipase B), *Thermomyces lanuginosus, Rhizomucor miehei, R. oryza, Rhizopus delemar*, etc.

Within the context of the present invention, the term "deodorization" means a steam distillation process in which steam is injected into an oil under conditions of high temperature (typically >200° C.) and high vacuum (typically <20 mBar) to remove volatile components like free fatty acids (FFA), fatty acid esters, mono- and diglycerides and to obtain an odorless oil composed of TAG.

Within the context of the present invention, the term "fractionation" means a separation process in which a certain quantity of a mixture (solid, liquid, suspension) is separated into fractions during a phase transition. These fractions vary in composition thus usually allowing enrichment of a species in one of the fractions and its subsequent separation and/or purification.

Within the context of the present invention, the term "selective precipitation" or "selective crystallization" indicates a separation and/or purification technique whereby the creation of one or several specific precipitates (solids) occur from a solution containing other potential precipitates by means of adapting the temperature of the precipitation. For example, the species having a melting point above the temperature of the precipitation process will not form a precipitate under those conditions. In one embodiment of the present invention, the selective precipitation results in crystallization of the desired product.

Within the context of the present invention, the term "immobilized form" means that the enzyme (i.e. lipase) is attached either covalently or non-covalently (e.g. adsorbed) to a solid carrier material. Non limiting examples of suitable carriers are: macroporous hydrophobic supports for covalent attachment made of methacrylate resins with, for example, epoxy, butyl or amino groups together with a suitable linker molecule (e.g. glutaraldehyde); for non-covalent immobilization through hydrophobic interactions via macroporous carriers made of, e.g., polystyrenic adsorbent, octadecyl methacrylate, polypropylene, non-compressible silica gel; for non-covalently adsorption via ionic interactions ionic exchange resins are used, e.g., polystyrenic ion exchange resin or silica.

Non limiting examples of sn-1,3 lipase in immobilized form are: lipase from *Thermomyces lanuginosis* adsorbed on silica (e.g., Lipozyme TL IM, Novozymes), lipase B from *Candida antarctica* adsorbed on methacrylate/divinylbenzene copolymer (e.g. Lipozyme 435, Novozymes), lipase from *Rhizomucor miehei* attached via ion exchange on styrene/DVB polymer (e.g., Novozym® 40086, Novozymes) or via hydrophobic interaction onto macroporous polypropylene (Accurel EP 100).

Synthetic Triglyceride Composition (Triglyceride Ingredient)

The triglyceride profile of human breast milk lipids has been further investigated by the inventors of the present invention who analysed human breast milk samples from European and Chinese lactating women and found the following results (see also Example A in the Experimental section):

| Name of analyte | European Human Milk % | Chinese Human Milk % |
|---|---|---|
| 18:1-16:0-18:1 | 13.9 | 13.8 |
| 18:1-16:0-18:2 | 5.95 | 13.8 |

US 12,564,198 B2

7

-continued

| Name of analyte | European Human Milk % | Chinese Human Milk % |
|---|---|---|
| 16:0-16:0-18:1 | 5.68 | 5.7 |
| 16:0-16:0-18:2 | 1.5 | 3.4 |
| 18:2-16:0-18:2 | <1 | 4.4 |
| 18:0-16:0-18:1 | 5.15 | 4 |
| 16:1-16:0-18:1 | 2.13 | 2.51 |
| 14:0-16:0-18:1 | 2.46 | 1.87 |
| 18:1-16:0-18:3 | <1 | 1.62 |
| 12:0-16:0-18:1 | 2.86 | 3.05 |
| 14:0-16:0-18:2 | <1 | 1.28 |
| 16:1-16:0-18:2 | <1 | 2.94 |
| 18:0-16:0-18:2 | <1 | 1.74 |
| 10:0-16:0-18:1 | 1.27 | 1.79 |

Based on discovered profile of triglycerides having a palmitic acid in sn-2, the inventors of the present application identified the need for a triglyceride ingredient comprising TAGs having 70% or more of the palmitic acid content esterified in the sn-2 position and triglyceride having palmitic acid in sn-2 position being present in a ratio as close as possible to the ratio at which they have been discovered to be present in human breast milk and above described.

Thus in one aspect, the present invention provides for a triglyceride ingredient comprising TAGs having 70% or more of the palmitic acid content esterified in the sn-2 position and comprising OPO (18:1-16:0-18:1) and OPL (18:1-16:0-18:2) triglycerides wherein the ratio between OPO and OPL triglycerides ranges from 1:0.3 to 1:1.5.

In one embodiment of the present invention, a triglyceride ingredient is provided comprising TAGs having 70% or more of the palmitic acid content esterified in the sn-2 position, comprising OPO (18:1-16:0-18:1) and OPL (18:1-16:0-18:2) triglycerides in a ratio between OPO and OPL triglycerides ranges from 1:0.3 to 1:1.5 and also additionally comprising at least one triglyceride selected in the group consisting of: PPO (16:0-16:0-18:1), SPO (18:0-16:0-18:1) and LaPO (12:0-16:0-18:1), wherein the ratio between OPO and each of such triglycerides when present ranges from 1:0.2 to 1:0.6 for PPO, from 1:0.05 to 1:0.5 for LaPO and from 1:0.05 to 1:0.5 for SPO.

In another embodiment, a triglyceride ingredient is provided comprising TAGs having 70% or more of the palmitic acid content esterified in the sn-2 position, comprising OPO (18:1-16:0-18:1) and OPL (18:1-16:0-18:2) triglycerides in a ratio between OPO and OPL triglycerides ranges from 1:0.3 to 1:1.5 and also additionally comprising PPO (16:0-16:0-18:1), SPO (18:0-16:0-18:1) and LaPO (12:0-16:0-18:1) triglycerides, wherein the ratio between OPO and each of such triglycerides when present ranges from 1:0.2 to 1:0.6 for PPO, from 1:0.05 to 1:0.5 for LaPO and from 1:0.05 to 1:0.5 for SPO.

In one embodiment of the present invention, a triglyceride ingredient is provided comprising TAGs having 70% or more of the palmitic acid content esterified in the sn-2 position, comprising OPO (18:1-16:0-18:1) and OPL (18:1-16:0-18:2) triglycerides in a ratio between OPO and OPL triglycerides ranges from 1:0.3 to 1:1.5 and also additionally comprising at least one triglyceride selected in the group consisting of: PPO (16:0-16:0-18:1), SPO (18:0-16:0-18:1), LaPO (12:0-16:0-18:1), OPM (18:1-16:0-14:0), OPPa (16:1-16:0-18:1), LPP (16:0-16:0-18:2), LPL (18:2-16:0-18:2) and LPPa (16:1-16:0-18:2), wherein the ratio between OPO and each of such triglycerides when present ranges from 1:0.2 to 1:0.6 for PPO, from 1:0.05 to 1:0.5 for LaPO, from 1:0.05 to 1:0.5 for SPO, from 1:0.05 to 1:0.3 for OPM, from 1:0.05 to 1:0.3 for OPPa, from 1:0.05 to 1:0.4 for LPP, from 1:0 to 1:0.5 for LPL and from 1:0 to 1:0.5 for LPPa.

In another embodiment, a triglyceride ingredient is provided comprising TAGs having 70% or more of the palmitic acid content esterified in the sn-2 position, comprising OPO (18:1-16:0-18:1) and OPL (18:1-16:0-18:2) triglycerides in a ratio between OPO and OPL triglycerides ranges from 1:0.3 to 1:1.5 and also additionally comprising PPO (16:0-16:0-18:1), SPO (18:0-16:0-18:1) and LaPO (12:0-16:0-18:1) OPM (18:1-16:0-14:0), OPPa (16:1-16:0-18:1), LPP (16:0-16:0-18:2), LPL (18:2-16:0-18:2) and LPPa (16:1-16:0-18:2) triglycerides, wherein the ratio between OPO and each of such triglycerides when present ranges from 1:0.2 to 1:0.6 for PPO, from 1:0.05 to 1:0.5 for La PO, from 1:0.05 to 1:0.5 for SPO, from 1:0.05 to 1:0.3 for OPM, from 1:0.05 to 1:0.3 for OPPa, from 1:0.05 to 1:0.4 for LPP, from 1:0 to 1:0.5 for LPL and from 1:0 to 1:0.5 for LPPa.

In one embodiment of the present invention the triglyceride ingredient comprises an amount of OPO ranging from 20 to 25%, an amount of OPL ranging from 20 to 25%, an amount of PPO ranging from 7 to 15%, an amount of SPO ranging from 1 to 5%, and an amount of LaPO ranging from 1 to 5%.

In one embodiment of the present invention the triglyceride ingredient comprises an amount of OPO ranging from 20 to 25%, an amount of OPL ranging from 10 to 25%, an amount of PPO ranging from 7 to 15%, an amount of SPO ranging from 1 to 5%, an amount of LaPO ranging from 1 to 5%, an amount of OPM ranging from 1% to 5%, an amount of OPPa ranging from 1 to 5%, and amount of LPP ranging from 0.5 to 7%, an amount of LPL ranging from 0 to 7% and an amount of LPPa ranging from 0 to 5%.

In one embodiment of the present invention, the triglyceride ingredient comprises triglycerides having palmitic acid in sn2 position in a ratio similar to that observed in samples of Chinese human breast milk.

In such embodiment, the triglyceride ingredient according to the present invention comprises an amount of OPO ranging from 20 to 25%, an amount of OPL ranging from 10 to 25%, an amount of PPO ranging from 7 to 15%, an amount of SPO ranging from 1 to 5%, an amount of OPLa ranging from 1 to 5%, an amount of OPM ranging from 1% to 5%, an amount of OPPa ranging from 1 to 5%, and amount of LPP ranging from 0.5 to 7%, an amount of LPL ranging from 2 to 7% and an amount of LPPa ranging from 0 to 5%.

In another embodiment of the present invention, the triglyceride ingredient of the present invention comprises triglycerides having palmitic acid in sn-2 position in a ratio similar to that observed in samples of European human breast milk.

Use of the Triglyceride Ingredient

In one aspect of the present invention, the use of a triglyceride ingredient according to the present invention is provided for preparing a fat blend to be incorporated in Infant formula products where it would represent at least a part of the Infant formula lipid fraction.

The triglyceride ingredient according to the present invention comprises TAGs having 70% or more of the palmitic acid content esterified in the sn-2 position and comprises specific TAGs having a palmitic acid at sn-2 position in ratios that resemble those occurring in human milk samples. By virtue of its nature, the sn-2 TAG ingredient of the present invention may be conveniently admixed with any vegetable oils (containing a minimum of palmitic acid residues) and suitable to be used in infant formula to allow the preparation of a fat blend for use in Infant formulas which would resemble the profile of TAG having palmitic acid in sn-2 position present in human breast milk.

Triglyceride Fat Blend

Accordingly, in one aspect the present invention also provides for a triglyceride fat blend which comprises TAGs having 70% or more of the palmitic acid content esterified in the sn-2 position and comprises specific TAGs having a palmitic acid at sn-2 position in ratios that resemble those occurring in human milk samples.

In one embodiment, the present invention provides for a triglyceride fat blend comprising TAGs having 70% or more of the palmitic acid content esterified in the sn-2 position and comprising OPO (18:1-16:0-18:1) and OPL (18:1-16:0-18:2) triglycerides wherein the ratio between OPO and OPL triglycerides ranges from 1:0.3 to 1:1.5.

In one embodiment of the present invention, a triglyceride fat blend is provided comprising TAGs having 70% or more of the palmitic acid content esterified in the sn-2 position, comprising OPO (18:1-16:0-18:1) and OPL (18:1-16:0-18:2) triglycerides in a ratio between OPO and OPL triglycerides ranges from 1:0.3 to 1:1.5 and also additionally comprising at least one triglyceride selected in the group consisting of: PPO (16:0-16:0-18:1), SPO (18:0-16:0-18:1) and LaPO (12:0-16:0-18:1), wherein the ratio between OPO and each of such triglycerides when present ranges from 1:0.2 to 1:0.6 for PPO, from 1:0.05 to 1:0.5 for LaPO and from 1:0.05 to 1:0.5 for SPO.

In another embodiment, a triglyceride fat blend is provided comprising TAGs having 70% or more of the palmitic acid content esterified in the sn-2 position, comprising OPO (18:1-16:0-18:1) and OPL (18:1-16:0-18:2) triglycerides in a ratio between OPO and OPL triglycerides ranges from 1:0.3 to 1:1.5 and also additionally comprising PPO (16:0-16:0-18:1), SPO (18:0-16:0-18:1) and LaPO (12:0-16:0-18:1) triglycerides, wherein the ratio between OPO and each of such triglycerides when present ranges from 1:0.2 to 1:0.6 for PPO, from 1:0.05 to 1:0.5 for LaPO and from 1:0.05 to 1:0.5 for SPO.

In one embodiment of the present invention, a triglyceride fat blend is provided comprising TAGs having 70% or more of the palmitic acid content esterified in the sn-2 position, comprising OPO (18:1-16:0-18:1) and OPL (18:1-16:0-18:2) triglycerides in a ratio between OPO and OPL triglycerides ranges from 1:0.3 to 1:1.5 and also additionally comprising at least one triglyceride selected in the group consisting of: PPO (16:0-16:0-18:1), SPO (18:0-16:0-18:1), LaPO (12:0-16:0-18:1), OPM (18:1-16:0-14:0), OPPa (16:1-16:0-18:1), LPP (16:0-16:0-18:2), LPL (18:2-16:0-18:2) and LPPa (16:1-16:0-18:2), wherein the ratio between OPO and each of such triglycerides when present ranges from 1:0.2 to 1:0.6 for PPO, from 1:0.05 to 1:0.5 for LaPO, from 1:0.05 to 1:0.5 for SPO, from 1:0.05 to 1:0.3 for OPM, from 1:0.05 to 1:0.3 for OPPa, from 1:0.05 to 1:0.4 for LPP, from 1:0 to 1:0.5 for LPL and from 1:0 to 1:0.5 for LPPa.

In another embodiment, a triglyceride fat blend is provided comprising TAGS having 70% or more of the palmitic acid content esterified in the sn-2 position, comprising OPO (18:1-16:0-18:1) and OPL (18:1-16:0-18:2) triglycerides in a ratio between OPO and OPL triglycerides ranges from 1:0.3 to 1:1.5 and also additionally comprising PPO (16:0-16:0-18:1), SPO (18:0-16:0-18:1) and LaPO (12:0-16:0-18:1) OPM (18:1-16:0-14:0), OPPa (16:1-16:0-18:1), LPP (16:0-16:0-18:2), LPL (18:2-16:0-18:2) and LPPa (16:1-16:0-18:2) triglycerides, wherein the ratio between OPO and each of such triglycerides when present ranges from 1:0.2 to 1:0.6 for PPO, from 1:0.05 to 1:0.5 for LaPO, from 1:0.05 to 1:0.5 for SPO, from 1:0.05 to 1:0.3 for OPM, from 1:0.05 to 1:0.3 for OPPa, from 1:0.05 to 1:0.4 for LPP, from 1:0 to 1:0.5 for LPL and from 1:0 to 1:0.5 for LPPa.

In one embodiment of the present invention the triglyceride fat blend comprises an amount of OPO ranging from 10 to 15%, an amount of OPL ranging from 10 to 15%, an amount of OPP ranging from 4 to 9%, an amount of OPS ranging from 0.5 to 3% and an amount of OPLa ranging from 0.5 to 3%.

In one embodiment of the present invention the triglyceride fat blend comprises an amount of OPO ranging from 10 to 15%, an amount of OPL ranging from 5 to 15%, an amount of OPP ranging from 4 to 9%, an amount of OPS ranging from 0.5 to 3% and an amount of OPLa ranging from 0.5 to 3%, an amount of OPM ranging from 0.5% to 3%, an amount of OPPa ranging from 0.5 to 3%, and amount of LPP ranging from 0.5 to 5%, an amount of LPL ranging from 0 to 5% and an amount of LPPa ranging from 0 to 5%.

In one embodiment of the present invention, the triglyceride fat blend comprises triglycerides having palmitic acid in sn2 position in a ratio similar to that observed in samples of Chinese human breast milk.

In such embodiment, the triglyceride fat blend according to the present invention comprises an amount of OPO ranging from 10 to 15%, an amount of OPL ranging from 10 to 15%, an amount of OPP ranging from 4 to 9%, an amount of OPS ranging from 0.5 to 3% and an amount of OPLa ranging from 0.5 to 3%, an amount of OPM ranging from 0.5% to 3%, an amount of OPPa ranging from 0.5 to 3%, and amount of LPP ranging from 0.5 to 5%, an amount of LPL ranging from 0 to 5% and an amount of LPPa ranging from 0 to 5%.

In another embodiment of the present invention, the triglyceride fat blend of the present invention comprises triglycerides having palmitic acid in sn2 position in a ratio similar to that observed in samples of European human breast milk.

Process for the Preparation of the Triglyceride Ingredient (sn-2 TAG Ingredient)

Alcoholysis [Step a)]

A challenge with selective alcoholysis of tripalmitin into 2-monopalmitin is the high melting point of tripalmitin (65° C.). As Chemical alcoholysis is non-specific, it can thus not be used to produce 2-monopalmitin. On the contrary, enzymatic alcoholysis can lead to a highly selective alcoholysis at the sn-1,3 positions making high purity synthesis of 2-monopalmitin possible.

The problem of using enzymes is the relatively poor thermostability of most of the commercial enzymes and results in lipase inactivation when reactions are performed at above 50° C. To minimize lipase inactivation and achieve full solubilization of the substrate (e.g. tripalmitin) at lower temperatures (<50° C.), organic solvents, most commonly acetone, n-hexane, or MTBE, are typically used. However, the use of solvents for industrial application increases the process complexity and operations (solvent removal and handling, safety), and thus drive the process costs (solvent cost, larger reaction volumes and thus equipment/reactors) as well as pose an environmental burden (solvent recycling).

In the context of the present invention, switching from the commonly used alcohols, methanol and ethanol, to n-butanol supplied at high molar ratio (15 equivalents) has surprisingly allowed the substrate to be solubilized at 50° C. without deactivating the enzyme, producing 2-monopalmitin with 90% purity.

In one embodiment of the present invention, the alcoholysis step a) is performed with n-butanol, n-pentanol, isopropanol or mixtures thereof.

In one embodiment of the present invention, the alcoholysis step a) is performed with an excess of n-butanol.

By using n-butanol in step a) (alcoholysis), the reaction proceeded without any solvent at 50° C. Butanol acts as both substrate and solubilization agent for the triglycerides, thereby, enabling a solvent-free reaction, high conversion yield (excess) and lipase activity.

In one embodiment of the present invention, the starting material for step a) is a triglyceride mixture enriched in palmitic acid at sn-2 position, such as for example Cristal-Green® (which is a commercially available product by Bunge Loders Croklaan).

In on embodiment of the present invention, step a) is performed at a temperature ranging from 40 to 70 deg C., for example at a temperature ranging from 45 to 55 deg C.

In one embodiment, step a) is performed in the presence of an sn-1,3 lipase selected in the group consisting of: lipase from *Thermomyces lanuginosis* adsorbed on silica (e.g., Lipozyme TL IM, Novozymes), lipase B from *Candida antarctica* adsorbed on methacrylate/divinylbenzene copolymer (e.g. Lipozyme 435, Novozymes) and lipase from *Rhizomucor miehei* attached via ion exchange on styrene/DVB polymer (e.g., Novozyme° 40086, Novozymes) or via hydrophobic interaction onto macroporous polypropylene (Accurel EP 100).

In another embodiment, step a) is performed in the presence of an sn-1,3 lipase which is a lipase from Thermomyces lanuginosis adsorbed on silica (e.g., Lipozyme TL IM, Novozymes).

In step a), immobilized enzyme preparation allows to properly disperse the lipase in non-aqueous media, such as fats and solvents, and enables the recovery and reuse making the process more cost efficient.

Accordingly, alcoholysis step as described in the present invention provides several advantages to the process according to the present invention, for example:

solvent-free reaction allows smaller reactor volumes (increased volumetric productivity), lowered process costs and omits safety handling aspects, removal and recycling of the solvent (solvent removal is especially important for an ingredient aimed at infant nutrition for quality and safety reasons);

Immobilized lipases, such as Lipozyme TL IM (Novozymes), are commercially available lipases accessible at industrial scale.

Intermediate Purification [step b)]

The two-step enzymatic process according to the present invention is more complex than conventional methods of producing OPO, e.g. single step acidolysis, yet, the moderate increase in complexity enables to improve the quality in the final product significantly, i.e. higher sn-2 palmitate content, making it more attractive for use in IF.

A two-step process requires the purification of the intermediate and it is important that the increase in quality is not offset by increase in cost potentially deriving from intermediate purification [step b)].

Current technologies for intermediate purification include molecular distillation, solvent crystallization, and chromatography but all these three methods are too costly for the targeted application and would benefit from improvement/simplification. For example, solvent fractionation methods typically require solvent use and low temperatures (<−10° C.).

According to the process of the present invention, the intermediate purification step b) may be performed by selective crystallization of 2-monopalmitin. The side product to be removed in this purification step is the product of the reaction of the alcohol (methanol, ethanol, butanol . . . ) with the fatty acids present in position 1,3 (mainly palmitic acid). The resulting esters have different melting points depending on the alcohol used. In particular, butyl palmitate has a lower melting point (17° C.) than methyl and ethyl palmitic esters (30° C. and 24° C. respectively), providing a larger difference in melting point between 2-monopalmitin (60° C.) and the side products to be removed. This higher difference is beneficial for the separation process. Such side products including the excess of alcohol used in the alcoholysis can be effectively removed after the alcoholysis step a) by fractionation of the crude product at temperatures ranging from 0 to 10° C., whereby the 2-monopalmitin undergoes selective crystallization and the side products remain in the liquid state and can be filtered off, for example.

Accordingly, fractionation temperatures above 0° C. of the crude products and no addition of solvents allows for a simple and cheap purification step of 2-monopalmitin.

Using solvent-free fractionation, the selective crystallization of the target product (2-monopalmitin) can be performed at higher temperature and there is no need to perform a step for solvent removal by distillation.

In one embodiment of the present invention, step b) is performed by decreasing the temperature of the reaction mixture to a temperature ranging from 0 to 10 deg C. yielding to fractionation via selective precipitation of 2-monopalmitine and by filtering off the supernatant.

Solvent-Free Esterification [Step c)]

Solvent free enzymatic esterification of 2-monopalmitin to form OPO has been described in literature before. In the study Highly selective synthesis of 1,3-Oleoyl-2-Palmitoylglycerol by Lipase Catalysis (Schmid et al, 1999) OPO was synthesized using sn-1,3 specific lipases from *Rhizomucor miehei* and *Rhizopus delemar* immobilized on different carrier materials. The reaction was performed at 50° C. with 3 equivalence of oleic acid and highly purified 2-monopalmitin (through solvent crystallization at −25° C.). 10-25% immobilized lipase based on weight of 2-monopalmitin was used and the authors state 78% OPO was obtained with 96% sn-2 palmitic acid using *Rhizopus delemar* lipase immobilized on macroporous polypropylene (EP 100) after 16 h reaction. However, the same study revealed the limited temperature stability (at 52° C.) of such immobilized *R. delemar* lipase and, in addition, much long reaction times were needed to reach high OPO concentrations during 2-monopalmitin esterification.

In pre-screening tests, pure 2-monopalmitin was used as starting material and three different immobilized lipases were evaluated; Lipozyme 435, Lipozyme TL IM, Novozymes 40145 NS. The most efficient lipases in forming TAGs were Novozymes NS 40 145 and TL IM.

Lipozyme TL IM was chosen as it had been proven the most effective in the butanolysis reaction.

Additionally, using the same lipase in both reaction steps makes the process more cost effective and allows reuse of the same immobilized enzyme preparation for both process steps a) and c). The full process from CristalGreen® to sn-2 TAG ingredient could be performed using only one lipase: Lipozyme TL IM.

In step c) immobilized enzyme preparation allows to properly disperse the lipase in non-aqueous media, such as fats and solvents, and enables the recovery and reuse making the process more cost efficient.

In one embodiment of the present invention, step c) is performed at a temperature ranging from 35 to 60 deg C., for example at a temperature ranging from 40 to 50 deg C.

In one embodiment, the immobilized lipase of step c) is a lipase derived from *Thermomyces lanuginosis* adsorbed on silica (for example Lipozyme TL IM from Novoyzmes).

In one embodiment, step c) is performed in the presence of a total of 2 to 3 equivalents (mole ratio) of a fatty acid mixture.

In one embodiment, the fatty acid mixture used in step c) to perform the esterification comprises 50-70% oleic acid, 25-30% linoleic acid, 1-3% myristic acid, 1-3% palmitoleic acid, 2-4% lauric acid and 2-4% stearic acid wherein such amounts are with respect to the total content of fatty acid mixture.

Deodorization [Step d)]

Deodorization of the final TAG product mixture deriving from step c) according to the process of the present invention may be performed as an optional purification step to remove the excess of free fatty acids, remaining fatty acid alkyl esters and mono- and di-glycerides.

Typically, deodorization of the mixture and/or product that needs to be purified may be performed at a temperature higher than >200° C. and under vacuum conditions of pressure lower than 20 mBar.

Experimental Section

Example A

Analysis of Human Breast Milk Samples from European and Chinese Lactating Women

The TAG profile in human breast milk samples from European and Chinese lactating women were analysed. The Rose-Gottlieb (ISO 1211) method was used as the reference method for the quantification of total lipids. In order to decrease the sample size needed for analysis, the method was slightly modified: sample size was decreased to 100 p.L and solvent volumes reduced in order to maintain the same proportions sample/solvent of the reference method. As internal standard solution, 1,3(d5)-dipalmitoyl-2-stearoyl-glycerol 0.4 Nino! L-lwas used. The analysis was performed as previously described [Nagy et al 2012, J. Lipid Res. 2013, 54, 290-305]. Briefly, chromatography separation was achieved with a liquid chromatograph equipped with an Agilent Poroshell 120 EC-C18 column (150×2.1 (i.d.) mm, 2.7 p.m: Agilent Technologies, Santa Clara, CA, USA). Solvent A consisted of n-hexane and isopropanol (1:1, v:v). Solvent B was 10 mmol L-1 ammonium-formate solubilized in methanol. An LTQ-Orbitrap Elite hybrid mass spectrometer (ThermoFisher Scientific) was used for identification of TAG regioisomers. The Orbitrap was operated at 30,000 resolution in a mass to charge ratio (m/z) between 200 and 1500. Data dependent events were produced according to an inclusion list including the accurate masses of ammoniated TAG and applying parent mass width criteria of ±5 ppm. The inclusion list for data-dependent acquisition was created by calculating the accurate mass for TAG obtained by the combination of the most abundant FA in human milk. The mass tag of m/z 4.95540 between ammoniated and sodiated adducts was used, but only the ammoniated adducts were fragmented. The peaks in the TAG product ion spectrum allowed the determinations of FA residues and their intensity allowed the determinations of FA regioisomeric position according to the mathematical model described previously.

Results of the analysis is reported in Table A below and show the complete TAG profile of the samples.

| Name of analyte | European Human Milk % | Chinese Human Milk % |
|---|---|---|
| 18:1-16:0-18:1 | 13.9 | 13.8 |
| 18:1-16:0-18:2 | 5.95 | 13.8 |
| 16:0-16:0-18:1 | 5.68 | 5.7 |
| 16:0-16:0-18:2 | 1.5 | 3.4 |
| 18:2-16:0-18:2 | <1 | 4.4 |
| 18:0-16:0-18:1 | 5.15 | 4 |
| 16:1-16:0-18:1 | 2.13 | 2.51 |
| 14:0-16:0-18:1 | 2.46 | 1.87 |
| 18:1-16:0-18:3 | <1 | 1.62 |
| 12:0-16:0-18:1 | 2.86 | 3.05 |
| 14:0-16:0-18:2 | <1 | 1.28 |
| 16:1-16:0-18:2 | <1 | 2.94 |
| 18:1-16:1-18:2 | 1.13 | 1.52 |
| 18:0-16:0-18:2 | <1 | 1.74 |
| 10:0-16:0-18:1 | 1.27 | 1.79 |

EXAMPLE 1

Production of 2-Monopalmitin Via Solvent-Free Alcoholysis Under Different Conditions Material and Methods Alcoholysis was performed on pure tripalmitin in solvent free conditions using isopropanol, n-butanol or and n-pentanol as alcohols.

The study was performed to assess the viability of solvent free alcoholysis of tripalmitin to produce 2-monopalmitin, using alcohols of chain length C3-05. For the process step to be viable, high conversions must be achieved to avoid the production of side products (e.g. diglycerides) that would impact the purification process and the reaction yield.

Equipment:

10×1.5 mL Agilent GC glass vials, screw-capped with septum

Thermomixer, with modified heating block to fit 1.5 mL Agilent GC-vials and temperature control Chemicals:

Tripalmitin, Glycerol Tripalmitate, 98%, Alfa Aesar, LOT #10184933

2-propanol, Honeywell, Chromasolv LC-MS

1-Butanol, Sigma-Aldrich, 99%

1-pentanol, Sigma-Aldrich, 99%

Alcohols were dried over molecular sieves (3 A) prior to experiment.

Enzymes:

Lipozyme 435, Novozymes, *Candida Antarctica* lipase B immobilized on hydrophobic carrier (acryl resin)

Lipozyme TL IM, Novozymes, *Thermomyces lanuginosus* lipase immobilized on silica gel carrier (non-compressible)

Procedure

Thermomixer was heated to 50° C.

175 mg tripalmitin was weighed into 1.5 mL glass vials with tight screw caps containing a rubber septum for sampling Alcohol was added to the vials and then the vials were closed The closed vials were placed in the thermomixer, shaken at 650 rpm until the substrate was fully dissolved Prior to reaction start (0 min), a sample (10 p.L) was taken Reaction was started by adding the lipase Samples were taken after 0, 30, 60, 120, 180 and 240 minutes Table 1 below reports lipases and alcohols used in the experiment and mass and volume in each reaction vial. Duplicate mixes were prepared, making a total of 10 vials prepared and tested.

TABLE 1

| | Lipase | | | Alcohol | |
|---|---|---|---|---|---|
| | | | | | Equivalence |
| Lipase | Mass (mg) | % w/w | Alcohol | Volume (µL) | (mol alcohol/ mol tripalmtin) |
| Lipozyme 435 | 15 | 12 | 2-propanol | 300 | 18 |
| Lipozyme 435 | 15 | 12 | n-butanol | 300 | 15 |
| Lipozyme TL IM | 30 | 17 | 2-propanol | 300 | 18 |
| Lipozyme TL IM | 30 | 17 | n-butanol | 300 | 15 |
| Lipozyme TL IM | 30 | 17 | n-pentanol | 300 | 13 |

Results and Discussion

Results show that enzymatic alcoholysis of model substrate could be performed solvent free with alcohols of chain length C3-05 using any of the lipase tested. The conversion yield of tripalmitin into 2-monopalmitin for each reaction were calculated for each sample point (and reported in FIG. 2). The best conversion yield achieved in the trial was 97%, using Lipozyme TL IM with n-butanol.

Tripalmitin was completely solubilized and miscible with the alcohols tested at 50° C.

As a preliminary test, alcoholysis had been performed in ethanol, solvent-free. Because of the high melting point of tripalmitin, the reaction temperature needed to be increased to 65° C. to have a solubilized tripalmitin but under these conditions only low conversion of tripalmitin into 2-monopalmitin could be observed (33%, in the presence of Lipozyme 435, Novozymes). Attempting to dissolve tri palmitin at 50° C. by adding larger volumes of ethanol worked only poorly as the lipid and the alcohol were not fully miscible, giving a turbid suspension, and no enzymatic conversion was observed.

Lipozyme TL IM

Higher yields were achieved using Lipozyme TL IM with the two alcohols: n-butanol and n-pentanol. The n-butanol reaction conversion reached its maximum after 2 h and the n-pentanol reaction after 3 h. The highest conversion achieved was with Lipozyme TL IM in n-butanol, reaching >95% after 2 h reaction. For Lipozyme TL IM, the reaction rates using isopropanol was lower than for the other two alcohols and the reaction didn't run to completion.

FIG. 3 shows the amount of tripalmitin, 1,2-dipalmitin and 2-monopalmitin expressed as molar fractions of the initial glyceride content. Shown is also the sum of the three fractions.

Lipozyme 435

The highest conversion achieved using Lipozyme 435 was below 50% after 3 h reaction with n-butanol. With isopropanol, Lipozyme 435 achieved higher reaction rates than Lipozyme TL IM. The highest conversion achieved with isopropanol was 40%, reached after 2 h reaction with Lipozyme 435.

EXAMPLE 2

Solvent-Free Butanolysis on a Fat High in sn-2 Palmitate by Lipozyme TL IM

Alcoholysis of a fat rich in sn-2 palmitate (CristalGreen°) was performed to produce 2-monopalmitin in solvent-free conditions with an industrially relevant starting material.

The experiment confirmed that CristalGreen® (similarly to tripalmitin) may be a viable source of sn-2 palmitate for enzymatic production of 2-monopalmitin in reaction conditions using n-butanol and Lipozyme TL IM.

Equipment:

500 mL Schott flask with screw-cap equipped and tubing for gas sparging

Magnetic stirrer, stirrer plate

Water bath with heater/temperature control

2×100 mL Schott flasks with rubber lined screw-caps

Adolf Kiihner Lab-Therm Lab shaker with temperature control Chemicals:

1-Butanol, Sigma-Aldrich, 99%, dried over molecular sieves (3A)

CristalGreen®

Enzymes:

Lipozyme TL IM, Novozymes, *Thermomyces lanuginosus* lipase immobilized on silica gel carrier (non-compressible)

Procedure:

Drying CristalGreen®

100 g CristalGreen® were weighed into a 500 mL Schott flask

Flask was placed in a water bath at 70° C. and sparged with nitrogen gas for 6 h.

Reaction (Duplicates)

To a 100 mL Schott flask was added:

10 g dried CristalGreen®

17 mL dry n-butanol

The flask was placed in a water bath at 70° C. until the fat was fully dissolved in butanol (clear, light yellow liquid)

The flask was placed in a Lab Shaker at 50° C. and 1400 rpm for 1 h 0 min sample was taken before reaction start (10 µL)

The reaction was started by adding 1.5 g Lipozyme TL IM

Samples were collected after 30, 60, 90, 120 and 150 minutes

Lipase Reusability

High enzyme stability and reusability is one important driver for process economy and costs in enzymatic processes. Recyclability of Lipozyme TL IM was tested during alcoholysis by removing (filtration) the lipase after reaching full conversion, transferring it into a fresh substrate solution and then comparing the conversion yield and product profile for three consecutive reactions.

Procedure:

Drying CristalGreen®

100 g CristalGreen® were weighed into a 500 mL Schott flask

Flask was placed in a water bath at 70° C. and sparged with nitrogen gas for 6 h.

Alcoholysis reaction was carried out in the same manner as described in example 2 i.e. 10 g dried Cristal Green were reacted with 17 mL n-butanol using 1.5 g Lipozyme TL IM as biocatalyst. The reaction was carried out for 2.5 h before being stopped. Then the reaction was stopped by filtering off the enzyme. The same enzyme was then reused in an identical reaction for three cycles. It was shown that it was possible to_reuse immobilized lipase TL in three alcoholysis reactions without losing its activity as similar product profiles were obtained for each reaction cycle.

Results and Discussion

Figure 4:
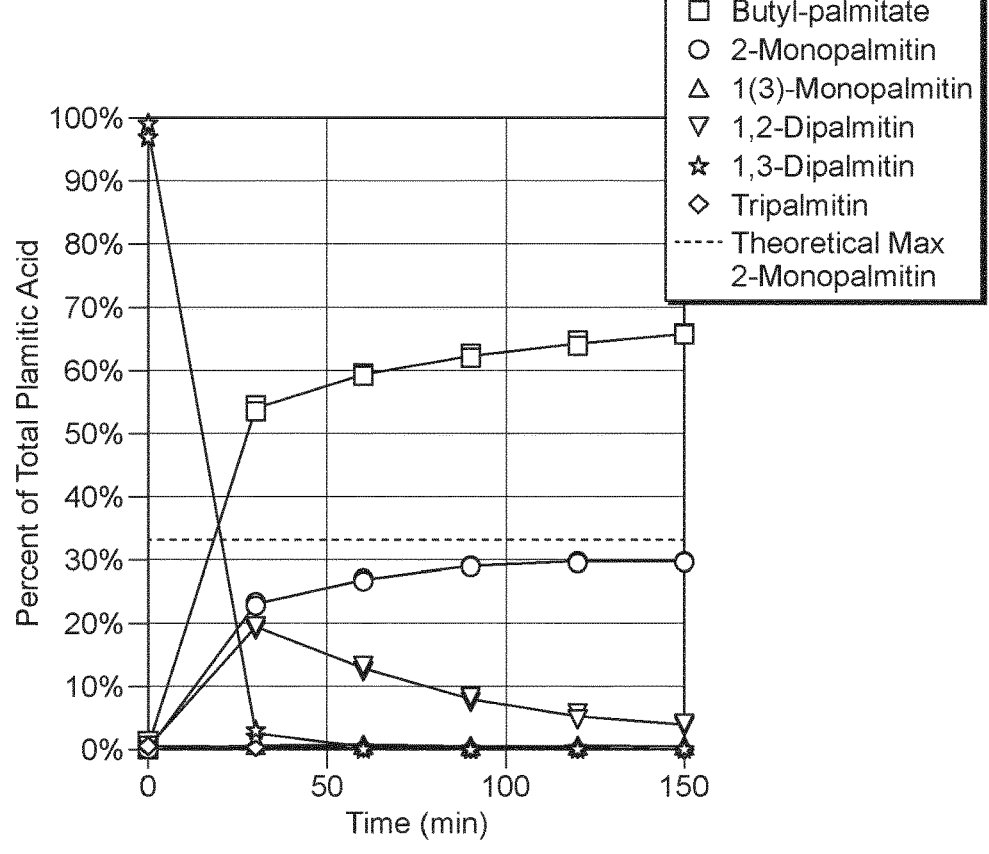
FIG. 4 shows each quantified species in the reaction mixture of Example 2 as a percentage of total quantified palmitic acid containing compounds.
Figure 5:
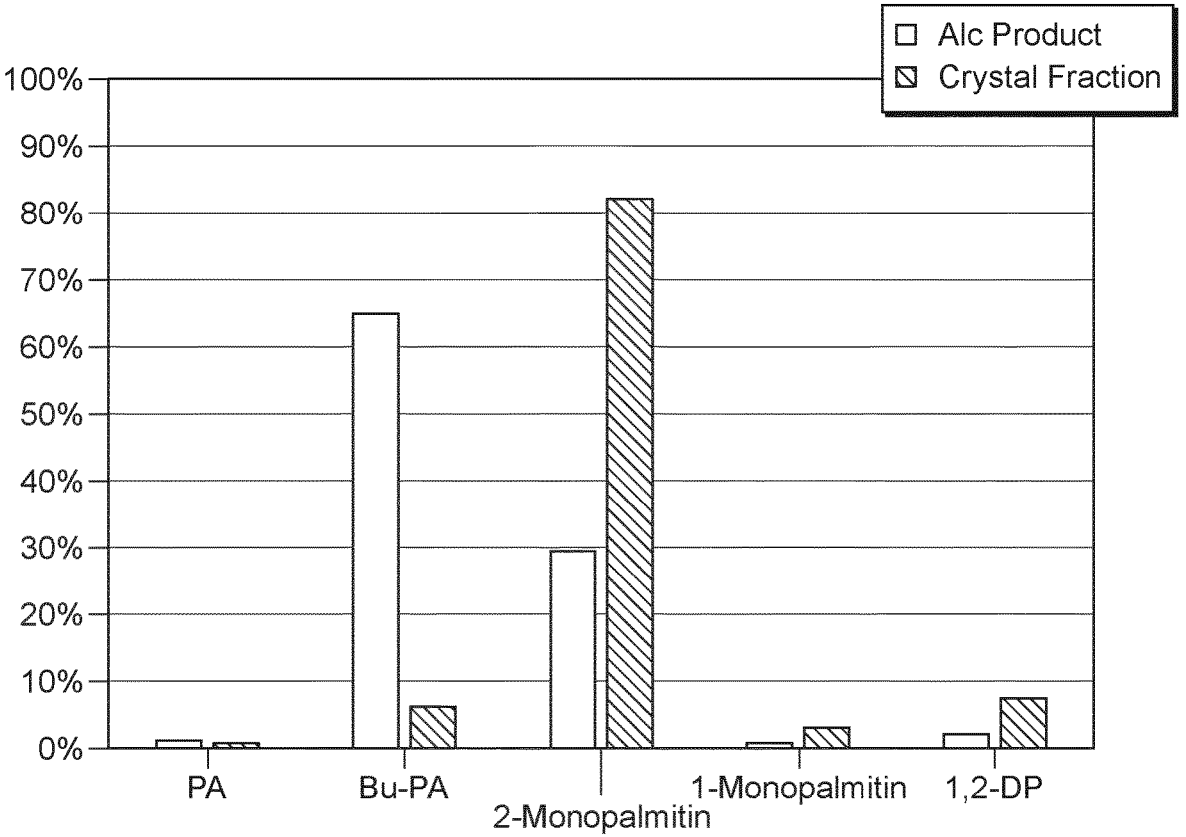
FIG. 5 shows content of alcoholysis product compared to the precipitate from fractionation of the same mix (Example 4)

The reaction progress of the alcoholysis reaction with CristalGreen® is shown in FIG. 4 and illustrates the depletion and formation of all species that contained palmitic acid (and were quantifiable by GC). The conversion of 2-monopalmitin from CristalGreen® in this solvent-free alcoholysis reaction amounted to 94%, based on the palmitic acid content in sn-2 position. The starting material Cristal-Green® contains 32% PA in sn-2 position (the other PA are located in sn-1 and/or 3) and 30% of these 32% PA were recovered in the final 2-monopalmitin product leading to a 94% conversion. The remaining 6% of PA not present in sn-2 position were found in the few side products, i.e. palmitic acid butyl ester and 1,2-DAG. The PA originally present in sn-1 and 3 of the starting material CristalGreen® were also converted into palmitic acid butyl ester.

EXAMPLE 3

Study of Purification of 2-Monopalmitin by Solvent Free Fractionation (Via Selective Precipitation)

2-monopalmitin was produced by n-butanolysis of CristalGreen® using Lipozyme TL IM as described in Example 2 and purified by solvent free fractionation via selective crystallization. To the 2-monopalmitin was added 2 equivalents of fatty acid alkyl ester and 13 equivalents of alcohol to create model mixtures for the study (as described below in Table 2). These mixes were then fractionated by gradually lowering the temperature in a water bath.

TABLE 2

| Palmitic acid Alkyl Ester | Weighed: (mg) | n: (mmol) | n(2-MAG) (mol) | (2-MAG) to weigh (mg): | n(alcohol) (mol) | m(alcohol) (mg) | V(alcohol) (mL) | V(alcohol) (μL) |
|---|---|---|---|---|---|---|---|---|
| Methyl- | 1058 | 3.91 | 1.96 | 645 | 0.0254 | 815 | 1.029 | 1029 |
| Ethyl- | 644 | 2.27 | 1.13 | 374 | 0.0147 | 679 | 0.860 | 860 |
| isopropyl- | 722 | 2.42 | 1.21 | 399 | 0.0157 | 946 | 1.203 | 1203 |
| n-butyl- | 600 | 1.92 | 0.96 | 317 | 0.0125 | 926 | 1.1444 | 1144 |
| n-pentyl- | 796 | 2.44 | 1.22 | 402 | 0.0159 | 1398 | 1.723 | 1723 |

Part I—Preparing Palmitic Acid Alkyl Esters

Fatty acid alkyl esters were prepared from palmitic acid and alcohols methanol, ethanol, isopropanol, n-butanol and n-pentanol. The reaction was run in MTBE for the methanol and ethanol reactions. The other reactions were run solvent free. Lipozyme 435 catalyzed the reactions.

Equipment

5×100 mL Schott flask with rubber lined screw-caps

Adolf Kühner Lab-Therm Lab shaker with temperature control

Buchi rotavapor—lab scale evaporator

Vacuum filtration setup

5×50 mL round flasks

One gram of palmitic acid was reacted using 1 gram of Lipozyme 435 in 10 mL alcohol for isopropanol, butanol, and pentanol. Methanol and ethanol preparations were performed with 1 mL alcohol and 10 ml MTBE. Molecular sieves (3A) were added to the mixtures for water removal.

The reaction was performed at 50° C. with a shaking of 1400 rpm. The reaction was started by adding the lipase and ran for 12 hours. The reaction was stopped by filtering off the lipase. After the reaction was stopped, the remaining alcohols and solvents were evaporated in a rotavapor.

The retained phase from the evaporation was transferred to clear 2 mL glass vials and weighed. The corresponding amounts of 2-monopalmitin and alcohol were calculated and added to the tubes as per Table 2.

Part II—Crystallization/Fractionation Behavior of Mixtures of Fatty Acid Alkyl Ester, 2-Monopalmitin and Various Alcohols The mixes prepared under Part I were placed in a water bath at 40° C. The temperature was then gradually lowered and the phase transitions of the mixes and precipitation behavior were observed for the following 5 mixtures (as per Table 2):

methyl palmitate+2-monopalmitate+methanol ethyl palmitate+2-monopalmitate+ethanol isopropyl palmitate+2-monopalmitate+isopropanol n-butyl palmitate+2-monopalmitin+n-butanol n-pentyl palmitate+2-monopalmitin+n-pentanol Melting Points:

2-monopalmitin: 65° C.

Methyl palmitate: 30° C.

Ethyl palmitate: 24° C.

n-propyl palmitate: 20.4° C.

n-butyl palmitate: 16.9° C.

Results and Discussion

As a result of the experiment, isopropyl-, n-butyl- and n-pentyl-mixtures could be fractionated, as 2-monopalmitin and 1,2-dipalmitin precipitated while the alcohol and its corresponding palmitic acid alkyl ester remained in solution. Methyl- and ethyl-mixes could not be fractionated.

The mixtures deriving from longer chain alcohols formed white crystals of 1,2-dipalmitin and 2-monopalmitin.

The mixtures deriving from shorter chain could not be fractionated but rather the whole mix solidified.

From these results, it can be inferred that using a longer chain alcohol in the alcoholysis step aids in fractionation and makes solvent free fractionation possible.

Accordingly, having a C3-05 alcohol gives the additional unexpected benefit of an simplified intermediate purification step for the desired product (2-monopalmitin).

EXAMPLE 4

Intermediate purification—Solvent-Free Fractionation Via Selective Crystallization of Product Mixture Obtained by Solvent-Free Butanolysis of CristalGreen®

This study was performed to purify 2-monopalmitin from the product of the alcoholysis step as described in Example 2 via solvent free fractionation via selective precipitation.

Equipment:

50 mL Erlenmeyer flask

Vacuum filtration setup with xxx glass filter

Chemicals:

From the alcoholysis step as described in Example 2, a final reaction mixture is obtained after 2.5 h reaction consisting of approximately 0.95 equivalences 2-monoglycerides, 0.05 eq. 1,2-diglycerides, 2 eq. fatty acid n-butyl esters, 13 eq. n-butanol n-heptane Procedure:

The alcoholysis reaction was stopped by filtering of the lipase

The filtrate was transferred to a 50 mL Erlenmeyer flask

The flask was placed at 4° C. overnight

Part of the fractionation mix was poured over the glass filter. The solution passes through, leaving a filter cake of white crystals. The crystals were washed by dripping heptane over them while still running the vacuum. The vacuum was then stopped and the crystals scraped off the filter.

The crystals were dried in a desiccator and weighed.

Recovered from the fractionation and filtration was 1.62 g crystal fraction.

The achieved overall process yield as described in Examples 2 and 4 was up to 50%.

Result and Discussion

Intermediate purification by fractionation via selective crystallization of 2-monopalmitin was successfully performed on the final reaction mix from butanolysis of CristalGreen®. The amount of butyl palmitate was reduced by 90%. This shows that the method is viable for separating 2-monopalmitin (crystals) from liquid butyl palmitate and butanol, for example, via filtration.

EXAMPLE 5

Solvent Free Esterification of 2-Monopalmitin Derived From Butanolysis for sn2 TAG Ingredient Production A 2-monopalmitin product obtained according to the procedure described in Example 4 was subjected to esterification process with a mixture of fatty acids to produce a triglyceride mix similar to that of human breast milk.

Equipment:

2×25 mm Pyrex glass tubes with rubber caps equipped with tubing for gas sparging Water bath with heater/temperature control Chemicals:

Oleic acid, 99%, Sigma-Aldrich, LOT #0000051240

Linoleic acid, 99%, Sigma-Aldrich, LOT #SLCC7896

Palmitoleic acid, 99%, Nu-Chek prep, LOT #U-40A-A25-b

Myristic acid, 99%, Nu-Chek prep, LOT #N-14A-F14-J

Lauric acid, 98%, Sigma-Aldrich, LOT #MKBX6772V 2-monopalmitin, produced through butanolysis of Crystal Green, purified by solvent free fractional crystallization Enzymes:

Lipozyme TL IM, Novozymes, silica gel carrier (non-compressible), Batch LA331755

In duplicates:

Water bath was heated to 45° C.

Added to each Pyrex 25 mm glass tube:

1 g 2-monopalmitin (prepared as described in Example 4)

A total of 2.6 equivalences fatty acids consisting of:

1.43 mL oleic acid (60%)

706 pl linoleic acid (30%)

45 p.L palmitoleic acid (2%)

35 mg myristic acid (2%)

45 mg lauric acid (3%)

65 mg stearic acid (3%)

Pyrex tubes were placed in the water bath with nitrogen gas sparing through the oil 2-monopalmitin/fatty acids mix until the mix turned clear, the 2-monopalmitin was fully solved 0 min sample was taken (10 p.L)

The reaction was started by addition of 250 mg Lipozyme TL IM

Samples were taken after 3 h reaction for LC-MS analysis

The TAG profile in the samples were analysed. The Rose-Gottlieb (ISO 1211) method was used as the reference method for the quantification of total lipids. In order to decrease the sample size needed for analysis, the method was slightly modified: sample size was decreased to 100 μL and solvent volumes reduced in order to maintain the same proportions sample/solvent of the reference method. As internal standard solution, 1,3(d5)-dipalmitoyl-2-stearoyl-glycerol 0.4 mol L$^{-1}$ was used. The analysis was performed as previously described [Nagy et al 2012, J. Lipid Res. 2013, 54, 290-305]. Briefly, chromatography separation was achieved with a liquid chromatograph equipped with an Agilent Poroshell 120 EC-C18 column (150×2.1 (i.d.) mm, 2.7 p.m: Agilent Technologies, Santa Clara, CA, USA). Solvent A consisted of n-hexane and isopropanol (1:1, v:v). Solvent B was 10 mmol L$^{-1}$ ammonium-formate solubilized in methanol. An LTQ-Orbitrap Elite hybrid mass spectrometer (ThermoFisher Scientific) was used for identification of TAG regioisomers. The Orbitrap was operated at 30,000 resolution in a mass to charge ratio (m/z) between 200 and 1500. Data dependent events were produced according to an inclusion list including the accurate masses of ammoniated TAG and applying parent mass width criteria of ±5 ppm. The inclusion list for data-dependent acquisition was created by calculating the accurate mass for TAG obtained by the combination of the most abundant FA in human milk. The mass tag of m/z 4.95540 between ammoniated and sodiated adducts was used, but only the ammoniated adducts were fragmented. The peaks in the TAG product ion spectrum allowed the determinations of FA residues and their intensity allowed the determinations of FA regioisomeric position according to the mathematical model described previously.

Results

The composition obtained was analysed and results for some of the obtained TAGS are reported below in Table 3. Results are expressed as g of TAG/100 g of total triglycerides in the obtained composition.

TABLE 3

| Name of analyte | % | Ratio to OPO |
|---|---|---|
| 18:1-16:0-18:1 | 23.29 | — |
| 18:1-16:0-18:2 | 22.59 | 0.96 |
| 16:0-16:0-18:1 | 11.29 | 0.49 |
| 18:0-16:0-18:1 | 2.72 | 0.12 |
| 16:0-16:0-18:2 | 5.86 | 0.25 |
| 18:2-16:0-18:2 | 5.50 | 0.23 |
| 16:1-16:0-18:1 | 1.98 | 0.08 |
| 14:0-16:0-18:1 | 1.77 | 0.07 |
| 16:1-16:0-18:2 | 0.62 | 0.02 |
| 12:0-16:0-18:1 | 2.43 | 0.10 |

The experiment indicated that, surprisingly, all the fatty acid added to the mixture could be incorporated into the obtained product in the presence of Lypozyme TL IM and that the ratio of the obtained TAGs having a palmitic acid residue in position sn2 reflect that observed in human milk samples according to the finding of the present inventors as reported in Example A.

EXAMPLE 6

Preparation of a Triglyceride Fat Blend with sn2 TAG Profile Similar to Chinese Human Breast Milk for Use in Infant Formula Starting From a Triglyceride Ingredient According to the Present Invention A triglyceride ingredient obtained according to the procedure described in Example 5 is admixed with a vegetable oil mix having low palmitic acid content consisting of e.g. pure or mixed rapeseed oil, high oleic sunflower oil, sunflower oil. The vegetable oil mix is added at 40% of the triglyceride ingredient achieving a dilution effect for the TAG that are present in the TAG Ingredient as the vegetable oil does not contain TAGs having a palmitic acid residue in position sn-2. The resulting triglyceride fat blend comprised:

| Name of analyte | % |
| --- | --- |
| 18:1-16:0-18:1 | 13.97 |
| 18:1-16:0-18:2 | 13.56 |
| 16:0-16:0-18:1 | 6.78 |
| 18:0-16:0-18:1 | 1.63 |
| 16:0-16:0-18:2 | 3.52 |
| 18:2-16:0-18:2 | 3.30 |
| 16:1-16:0-18:1 | 1.19 |
| 14:0-16:0-18:1 | 1.06 |
| 16:1-16:0-18:2 | 0.37 |
| 12:0-16:0-18:1 | 1.46 |

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. A triglyceride ingredient comprising synthetic TAGs having 70% or more of the palmitic acid content esterified in the sn-2 position and comprising OPO (18:1-16:0-18:1) triglyceride and OPL (18:1-16:0-18:2) triglyceride, wherein the ratio between the OPO triglyceride and the OPL triglyceride ranges from 1:0.3 to 1:1.5, and the triglyceride ingredient further comprises OPM (18:1-16:0-14:0) and at least one additional triglyceride selected from the group consisting of PPO (16:0-16:0-18:1), SPO (18:0-16:0-18:1), LaPO (12:0-16:0-18:1), OPPa (16:1-16:0-18:1), LPP (16:0-16:0-18:2), LPL (18:2-16:0-18:2) and LPPa (16:1-16:0-18:2), wherein the ratio between the OPO triglyceride and each of the at least one additional triglycerides when present ranges from 1:0.2 to 1:0.6 for PPO, from 1:0.05 to 1:0.5 for LaPO, from 1:0.05 to 1:0.5 for SPO, from 1:0.05 to 1:0.3 for OPM, from 1:0.05 to 1:0.3 for OPPa, from 1:0.05 to 1:0.4 for LPP, from 1:0 to 1:0.5 for LPL and from 1:0 to 1:0.5 for LPPa.

2. The triglyceride ingredient according to claim 1, which comprises PPO (16:0-16:0-18:1), SPO (18:0-16:0-18:1) and LaPO (12:0-16:0-18:1) OPM (18:1-16:0-14:0), OPPa (16:1-16:0-18:1), LPP (16:0-16:0-18:2), LPL (18:2-16:0-18:2) and LPPa (16:1-16:0-18:2) triglycerides.

3. The triglyceride ingredient according to claim 1, which comprises an amount of OPO ranging from 20 to 25% of total triglycerides in the ingredient, an amount of OPL ranging from 10 to 25%, an amount of OPP ranging from 7 to 15%, an amount of OPS ranging from 1 to 5%, an amount of OPLa ranging from 1 to 5%, an amount of OPM ranging from 1% to 5%, an amount of OPPa ranging from 1 to 5%, and amount of LPP ranging from 0.5 to 7%, an amount of LPL ranging from 2 to 7% and an amount of LPPa ranging from 0 to 5%.

4. A process for preparation of the triglyceride ingredient of claim 1, the process comprising:

subjecting tripalmitin and/or triglycerides enriched in palmitic acid at sn-2 position to an alcoholysis step performed in a composition comprising an immobilized lipase and a primary or secondary alcohol of chain length C3-C5, to produce a first product mixture comprising 2-monopalmitin;

purifying the first product mixture comprising 2-monopalmitin from step a) by fractionation process via selective crystallization of the 2-monopalmitin and subsequent removal of a remaining liquid fraction that is supernatant, to produce a second product mixture; and subjecting the second product mixture from step b) to an esterification step with a mixture of fatty acids, to produce the triglyceride ingredient of claim 1.

* * * * *